United States Patent [19]

Knoll et al.

[11] Patent Number: 4,822,604

[45] Date of Patent: Apr. 18, 1989

[54] LOCAL TREATMENT OF DANDRUFF, SEBORRHEIC DERMATITIS, AND PSORIASIS

[75] Inventors: Donald W. Knoll, Waukesha; David L. Shelton; Thomas J. Szymczak, both of Racine County, all of Wis.

[73] Assignee: S. C. Johnson & Son, Inc., Racine, Wis.

[21] Appl. No.: 736,011

[22] Filed: May 20, 1985

[51] Int. Cl.4 .............................................. A61K 7/06
[52] U.S. Cl. ............................. 424/70; 424/DIG. 4; 514/864; 514/880; 514/881
[58] Field of Search ........................... 424/DIG. 4, 70

[56] References Cited

U.S. PATENT DOCUMENTS

| | | | |
|---|---|---|---|
| 2,697,113 | 12/1954 | Lundsted et al. | 260/584 |
| 2,697,118 | 12/1954 | Lundsted | 546/477 |
| 3,149,042 | 9/1964 | Habicht et al. | 424/70 |
| 3,560,614 | 2/1971 | Embring | 424/70 |
| 3,642,977 | 2/1972 | Hewitt et al. | 424/70 |
| 3,700,601 | 10/1972 | Bloching | 252/105 |
| 3,935,129 | 1/1976 | Jabalee | 252/525 |
| 4,087,550 | 5/1978 | Bouillon et al. | 424/DIG. 4 |
| 4,243,543 | 1/1981 | Guilbert et al. | 252/105 |
| 4,295,985 | 10/1981 | Petrow et al. | 252/105 |
| 4,438,096 | 3/1984 | Preston | 424/70 |

FOREIGN PATENT DOCUMENTS

| | | | |
|---|---|---|---|
| B-8001 | 5/1982 | Australia | 424/70 |
| 2039408 | 2/1971 | Fed. Rep. of Germany | 424/70 |
| 1617632 | 4/1971 | Fed. Rep. of Germany | 424/70 |
| A-3101011 | 7/1982 | Fed. Rep. of Germany | 424/70 |
| 599634 | 1/1959 | Italy | 424/70 |
| 0025898 | 2/1984 | Japan | 424/70 |
| 1177511 | 1/1970 | United Kingdom | 424/70 |
| 1198005 | 7/1970 | United Kingdom | 424/95 |
| 1286919 | 8/1972 | United Kingdom | 424/70 |

OTHER PUBLICATIONS

"Handbuch der Kosmetika und Riechstoffe"—H. Janistyn, vol. III Die Korperpflegemittel, 2nd ed., pp. 256–257, 1973 (English translation included).

Primary Examiner—Dale R. Ore

[57] ABSTRACT

A clear, therapeutic hair care composition is presented having a low pH and useful in the local treatment of dandruff, seborrheic dermatitis and psoriasis of the scalp which resists oxidative decomposition. The shampoo is comprised of a detergent shampoo base, a therapeutic amount of a keratolytic agent and a keratolytic stabilizing agent to stabilize the keratolytic agent against oxidative decoloration decomposition catalyzed by ultraviolet radiation exposure. The keratolytic agent is preferably a salicylate and preferably salicylic acid and the keratolytic stabilizing agent is a tertiary amine.

12 Claims, No Drawings

LOCAL TREATMENT OF DANDRUFF, SEBORRHEIC DERMATITIS, AND PSORIASIS

BACKGROUND OF THE INVENTION

1. Field of the Invention

This invention relates to a clear, therapeutic hair care composition having low pH for use in local treatment of dandruff, seborrheic dermatitis, and psoriasis of the scalp which resists decoloration due to oxidative decomposition.

This invention further relates a clear, therapeutic hair care composition having low pH for use in local treatment of dandruff, seborrheic dermatitis, and psoriasis of the scalp which contains a detergent shampoo base, a therapeutic amount of keratolytic agents and keratolytic stabilizing agents in an amount sufficient to stabilize the keratolytic agents against decoloration decomposition from oxidation.

This invention further relates to a method to create a clear, therapeutic hair care composition having low pH which resists decomposition due to oxidation.

Other objects of this invention become apparent to those ordinarily skilled in the art from the reading of the description of the preferred embodiment.

2. Description of the Prior Art

Salicylic acid for use as a keratolytic agent in hair care compositions for the local treatment of dandruff, seborrheic dermatitis, and psoriasis of the scalp is old and well known in the art. However, use of salicylic acid as a keratolytic agent in shampoos designed for use in the local treatment of dandruff, seborrheic dermatitis, and psoriasis of the scalp entails certain drawbacks. Among these are decomposition of the keratolytic agent, namely the salicylic acid, by ultraviolet radiation induced oxidative decomposition. The decomposition causes the shampoo to change colors which is not at all desirable for a shampoo. Accordingly, all such products are packaged in opaque containers such that the effects of ultraviolet radiation-catalyzed oxidative decomposition are diminished if not completely removed. The shampoo is protected from exposure to ultraviolet radiation by the container itself and the shampoo, being opaque in color, masks the decomposition of the salicylic acid, which is the keratolytic agent, and so the consumer never really is aware whether or not the shampoo is effective in the local treatment of the nonexudative seborrheas of the scalp condition which prompted him to buy and use the product in the first place.

The use of a stabilizing agent for the keratolytic agent is also a desirable and well known accomplishment of the prior art. Many such stabilizing agents have been proposed such as those entailed in Petrow et al. U.S. Pat. No. 4,295,985. Petrow et al. discloses the use of kera-alkali metal thiosulfates in shampoos which act as reducers in the composition and would be candidates for stabilizers of the keratolytic agent, namely salicylic acid.

Tertiary amines are also generally susceptible to oxidation by mild oxidating agents and would serve as chelating agents to prevent the reduction of the salicylic acid. U.S. Pat. No. 2,697,118 describes N,N,N',N'-tetrakis (2-hydroxyproply) ethylenediamine, the crosslinking agent and catylist in rigid type polyurethane foams. This compound was found to form stable metal ion complexes with such cationic ions AjI, PbII, HgII, CuII, cadmium, cobolt, nickel and zinc. However, none of the prior art, insofar as we are able to determine, has recognized the use of tertiary amines as chelating agents or reducing agents to stabilize salicylic acid and other siliciates in a shampoo composition for use in the local treatment of dandruff, seborrheic dermatitis, and psoriasis of the scalp. Moreover, it has been found, that by use of the tertiary amines, it is possible to form a stable clear hair care composition having a low pH for use in the local treatment of dandruff, seborrheic dermatitis, and psoriasis of the scalp which resists decomposition, i.e. discoloration catalyzed by ultraviolet radiation exposure. It has been found that by the use of the tertiary amines in conjunction with other salicylic acids tabilizers, the production of a clear anti-dandruff shampoo is now possible which hereto before had been an impossibility.

SUMMARY OF THE INVENTION

This invention relates to a clear therapeutic hair care composition having a low pH for use in local treatment of dandruff, seborrheic dermatitis, and psoriasis of the scalp. The therapeutic hair care composition of this invention is comprised of a detergent shampoo base, a therapeutic amount of keratolytic agents and a keratolytic stabilizing agent in an amount sufficient to stablize the keratolytic agents against discoloration decomposition catalyzed by ultraviolet radiation exposure. The shampoo base is preferably a sulfated alcohol shampoo containing keratolytic agents as salicylate compounds and preferably salicylic acid.

The stabilizing agents are selected from the group consisting of tertiary amines, ascorbic acid, sodium sulfite, and other alkalyne metal stabilizers. The pH of the composition is within the range of about 3 to 6.5 and more preferably from 4.9 to 5.7. The keratolytic agent, which is a salicylate is present in an amount of about 1 to 3% by weight of the composition and more preferably 1.8 to 3.0%. The keratolytic stabilizing agents are present in an amount of 0.1 to 20% by weight and the tertiary amines is present in an amount of 0.25 to 20% by weight of the composition and more preferably 0.25 to 5% by weight of the composition. It has been found that this tertiary amine serves to stabilize the salicylic acid by acting as a reducing agent so that upon exposure to ultraviolet radiation, the salicylic acid does not decompose and discolor the shampoo. Thus, the use of keratolytic stabilizing agents, the salicylic acid and related salicylates are effective over a longer shelf life and may be packaged in clear containers which are most desirable from the consumers point of view. In addition, it has been found that it is possible by use of these keratolytic stabilizing agents to create a clear anti-dandruff shampoo which resists discoloration upon ultraviolet radiation exposure, which had hereto before been considered impossible.

This invention also relates to a method of stabilization of salicylic acid in hair care composition such that it resists discoloration and oxidative decomposition catalyzed by exposure to ultraviolet radiation. The method entails the addition of tertiary amines to a therapeutic shampoo base such that the tertiary amines act as reducing agents to prevent the decomposition of the salicylic acid upon exposure to ultraviolet radiation.

DETAILED DESCRIPTION OF THE PREFERRED EMBODIMENTS

Detergent shampoo base compositions containing therapeutic amounts of keratolytic agents used in the local treatment of dandruff, seborrheic dermatitis, and psoriasis of the scalp which have traditionally suffered from the shortcoming that exposure to ultraviolet radiation catalizes an oxidative decomposition in the keratolytic agent so that the composition changes colors and loses its effectiveness as a therapeutic composition.

It has been found that by the addition of a tertiary amine, ultraviolet radiation has minimal effect upon the keratolytic agent in the dandruff composition which is usually salicylic acid or some other salicylate. This finding has made it possible to produce a clear therapeutic hair care composition having a low pH for use in the local treatment of dandruff, seborrheic dermatitis, and psoriasis of the scalp which resist decoloration decomposition due to ultraviolet radiation exposure. The composition of the present invention is comprised of a detergent shampoo base selected from the group consisting of alpha olefin sulfonate, betaines, sarcosinates, sulfosuccinate, and a sulfated alcohol shampoo base such as are know in the prior art. A therapeutic amount of keratolytic agents selected from the group consisting of salicylic acid, magnesium salicylate, sodium salicylate, mixtures thereof, and the like are added to the shampoo base and keratolytic stabilizing agents selected from the group consisting of tertiary amines, ascorbic acid, sodium sulfite, sodium bisulfite, sodium thiosulfate, parabens, mixtures thereof, and the like added in amounts sufficient to stabilize the keratolytic agents against decoloration decomposition from ultraviolet radiation exposure. The pH of the composition is usually in the range of about 3 to 6.5 and more preferably in the range of about 4.9 to 5.7. The only limiting factor on the low end of the pH of the composition is that of the salicylic acid itself. Specifically, salicylic acid has a pH of about 3 where it can be seen that the shampoo base can have any pH within the range specified and the only limitation is that the entire composition have a pH of at least 3.

The keratolytic agent, most preferably salicylic acid, is most preferably present in an amount of about 1.8 to 3% by weight of the composition. It has been determined that this is the amount that is therapeutically effective and in compliance with all FDA guidelines relative to this ingredient. The keratolytic stabilizing agents would be present in an amount of from about 0.1 to about 20% by weight of the composition. When determining the exact composition of the keratolytic agents, it should be kept in mind that the tertiary amines are the main constituent of the keratolytic stabilizing agents and need to be in the composition in an amount of at least 0.25% by weight of the composition and most preferably in an amount of about 0.25 to 5.0% by weight of the composition and may be present in amounts of up to 0.25 to 20% by weight of the composition. The additional stabilizing agents, notably ascorbic acid, sodium sulfite, sodium bisulfite, sodium thiosulfate, parabens, and any mixture thereof are present in ranges from 0.1% to 20% and most preferably from 0.1 to 0.2% by weight of the composition.

The tertiary amines are selected from the group consisting N,N,N',N'-tetrakis (2-hydroxyproply) ethylenediamine, triethanol amine (TEA), tripropanol amine, tributanol amine, mixtures thereof and the like. The function of these amines is to act as a reducing agent for salicylic acid. The tertiary amine is structurally related to the EDTA family of chelating agents and is structurally susceptible to oxidation by mild oxidizing agents, such, that it acts as a reducing agent for salicylic acid.

The keratolytic agent N,N,N',N'-tetrakis (2-hydroxypropyl) ethylenediamine is described in U.S. Pat. No. 2,697,118, incorporated herein by reference, and is available from the BASF Wyandotte Corporation under the tradename "QUADROL".

In preparation of the composition of the present invention, a detergent shampoo base, and most preferably a sulfated alcohol shampoo base such as is conventional in the prior art is prepared in a conventional manner with various fragrances and color dyes such as are well know and cosmetically acceptable. A detergent base is added at least 0.25% tertiary amine more preferably in the range of 0.25 to 20% and most preferably in the range of 0.25 to 5% to the shampoo base. A keratolytic agent which is preferably salicylic acid is added to the composition in an amount of about 1.8 to 3.0% by weight of the composition. The resulting shampoo hair care composition is a clear therapeutic hair composition having a low pH for use in local treatment of dandruff, seborrheic dermatitis, and psoriasis of the scalp which resist decoloration due to ultraviolet radiation decomposition.

The following examples are provided to illustrate various formulations of the composition of the present invention and are not to be construed as limiting the invention.

| Ingredient | A | B | C | D |
|---|---|---|---|---|
| ALS—ALES | 55.00 | 55.00 | 70.00 | 70.00 |
| Cocamdidopropyl Betaine | 5.00 | — | 7.00 | 15.00 |
| Stearamide DEA | — | 2.50 | 2.50 | — |
| Salicylic Acid | 2.00 | 2.00 | 2.00 | 2.00 |
| Fragrance | 0.50 | 0.50 | 0.50 | 0.50 |
| FD & C Blue #1 | 0.00029 | 0.00009 | 0.00009 | 0.00029 |
| FD & C Yellow #5 | 0.00021 | 0.00004 | 0.00004 | 0.00021 |
| Sodium Hydroxide | 0.37 | 0.27 | 0.25 | 0.37 |
| Ammonium Chloride | 1.00 | 1.50 | 0.75 | — |
| D.I. Water | Q.S. | Q.S. | Q.S. | Q.S. |
| Birch Extract | 0.10 | 0.10 | 0.10 | 0.10 |
| Kathon CG | 0.02 | 0.02 | 0.01 | 0.01 |
| Triethanolamine | 0.25 | — | — | — |
| Ascorbic Acid | 0.014 | — | — | — |
| Sodium Bisulfite | — | 1.00 | — | — |
| Sodium Thiosulfate | — | — | 1.00 | — |
| Quadrol | — | — | — | 0.50 |
| Methylparaben | — | — | — | 0.10 |
| Propylparaben | — | — | — | 0.10 |

ALS—ALES — Ammonium Lauryl Sulfate/Ammonium Laureth Sulfate (27.5% active)
Kathon CG — Methylchloroisothiazolinone/methylisothiazolinone (1.5% active)
DEA — Diethanolamine All of the invention as described herein relates to a hair care composition, other compositions useful in the treatment of dandruff, seborrheic dermatitis, and psoriasis of the skin which are clear and have a low pH which resists decoloration due to exposure to ultraviolet radiations are included in the broad scope and spirit of the appended claims without departing from the scope and spirit of the invention as described herein.

We claim:

1. A clear therapeutic hair care composition having low pH for use in local treatment of dandruff, seborrheic dermatitis, and psoriasis of the scalp which resists oxidative decomposition, comprising:

(a) a detergent shampoo base;
(b) about 1.8 to 3.0% by weight of the composition of salicylate compound keratolytic agents selected from the group consisting of salicylic acid, acetyl salicylic acid, magnesium salicylate, sodium salicylate, and mixtures thereof; and
(c) about 0.25 to 20% by weight of the composition of a tertiary amine keratolytic stabilizing agent selected from the group consisting of N,N,N',N'-tetrakis(2-hydroxypropyl)ethylenediamine, triethanolamine, tripropanolamine, tributanolamine, and mixtures thereof wherein said keratolytic stabilizing agents are present in an amount sufficient to stabilize the keratolytic agents against oxidative decoloration decomposition catalyzed by ultraviolet radiation exposure.

2. The hair care composition of claim 1 wherein said shampoo base is a sulfated alcohol shampoo.

3. The hair care composition of claim 1 wherein the pH of the composition is in the range of about 3.0 to 6.5.

4. The hair care composition of claim 3 wherein the pH of the composition is about 4.9 to 5.7.

5. The hair care composition of claim 4, wherein said tertiary amine is N,N,N',N'-tetrakis(2-hydroxypropyl) ethylenediamine.

6. The hair care composition of claim 5, wherein said tertiary amine is present in an amount of about 0.25–5% by weight of the composition.

7. A method for treating dandruff, seborrheic dermatitis, and psoriasis of the scalp with a clear therapeutic hair care composition having low pH which resists decomposition from ultraviolet radiation comprising: contacting the scalp and hair with a composition comprising
(a) a detergent shampoo base;
(b) about 1.8 to 3.0% by weight of the composition of salicylate compound keratolytic agents selected from the group consisting of salicylic acid, acetyl salicylic acid, magnesium salicylate, sodium salicylate, and mixtures thereof; and
(c) about 0.25 to 20% by weight of the composition of a tertiary amine keratolytic stabilizing agent selected from the group consisting of N,N,N',N'-tetrakis(2-hydroxypropyl) ethylenediamine, triethanolamine, tripropanolamine, tributanolamine, and mixtures thereof wherein said keratolytic stabilizing agents are present in an amount sufficient to stabilize the keratolytic agents against oxidative decoloration decomposition catalyzed by ultraviolet radiation exposure.

8. The method of claim 7 wherein said shampoo base is a sulfated alcohol shampoo.

9. The method of claim 7 wherein the pH of the composition is in the range of about 3.0 to 6.5.

10. The method of claim 9 wherein the pH of the composition is about 4.9 to 5.7.

11. The method of claim 10, wherein said tertiary amine is (N,N,N',N'-tetrakis(2-hydroxypropyl) ethylenediamine.

12. The method of claim 11, wherein said tertiary amine is present in an amount of about 0.25 to 5% by weight of the composition.

* * * * *